United States Patent [19]

Bell

[11] Patent Number: 5,125,415
[45] Date of Patent: Jun. 30, 1992

[54] SYRINGE TIP CAP WITH SELF-SEALING FILTER

[75] Inventor: Craig J. Bell, Winchester, N.H.

[73] Assignee: Smiths Industries Medical Systems, Inc., Keene, N.H.

[21] Appl. No.: 540,159

[22] Filed: Jun. 19, 1990

[51] Int. Cl.⁵ .............................................. A61B 5/00
[52] U.S. Cl. .................................... 128/766; 604/190; 604/199; 604/403; 215/DIG. 3
[58] Field of Search ............... 604/126, 256, 236, 238, 604/190, 122, 403, 405, 406, 199; 128/763, 765, 766, 760; 215/261, 216, 364, 308, DIG. 3

[56] References Cited

U.S. PATENT DOCUMENTS

| | | | |
|---|---|---|---|
| 3,954,623 | 5/1976 | Hammer et al. | 210/436 |
| 3,978,846 | 9/1976 | Bailey | 128/762 |
| 4,043,334 | 8/1977 | Brown et al. | 604/199 |
| 4,085,737 | 4/1978 | Bordow | 128/763 |
| 4,157,967 | 6/1979 | Meyst et al. | 210/449 |
| 4,266,559 | 5/1981 | Akhavi | 128/766 |
| 4,317,455 | 3/1982 | Akhavi | 128/765 |
| 4,340,067 | 7/1982 | Rattenborg | 128/763 |
| 4,369,781 | 1/1983 | Gilson et al. | 604/403 |
| 4,424,817 | 1/1984 | Williams | 128/766 |
| 4,448,206 | 5/1984 | Martell | 128/765 |
| 4,466,446 | 8/1984 | Baidwan et al. | 128/765 |
| 4,573,977 | 3/1986 | Crawford | 604/212 |
| 4,595,021 | 7/1986 | Shimizu et al. | 128/765 |
| 4,597,758 | 7/1986 | Aalto et al. | 604/256 |
| 4,675,017 | 6/1987 | Sato | 604/405 |
| 4,685,472 | 8/1987 | Muto | 604/256 |
| 4,743,243 | 5/1988 | Vaillancourt | 604/405 |
| 4,755,170 | 7/1988 | Golden | 604/52 |
| 4,769,026 | 9/1988 | Strung | 604/415 |
| 4,775,376 | 10/1988 | Strung | 604/415 |
| 4,781,683 | 11/1988 | Wozniak et al. | 604/110 |
| 4,863,051 | 9/1989 | Eibner et al. | 215/261 |
| 4,957,501 | 9/1990 | Lahille et al. | 606/200 |

FOREIGN PATENT DOCUMENTS

| | | |
|---|---|---|
| 0060385 | 2/1982 | European Pat. Off. |
| 00081655 | 10/1982 | European Pat. Off. |
| 0321358 | 12/1988 | European Pat. Off. |
| 2605694 | 8/1977 | Fed. Rep. of Germany |
| 2176710A | 6/1985 | United Kingdom |

Primary Examiner—Max Hindenburg
Assistant Examiner—Guy V. Tucker
Attorney, Agent, or Firm—Sewall P. Bronstein; Robert M. Asher

[57] ABSTRACT

A syringe tip cap and a method for purging air from a syringe-like container containing air and hazardous liquid. The cap contains a hydrophilic filter which, when dry, allows air to pass through the filter. When the air is purged from the syringe, liquid from the container is pushed or drawn to the filter. The filter expands when wetted, seals the cap, and prevents further fluid flow. A flow restrictor may be included within the cap to concentrate the flow to only a portion of the filter to prevent premature sealing of the filter.

24 Claims, 1 Drawing Sheet

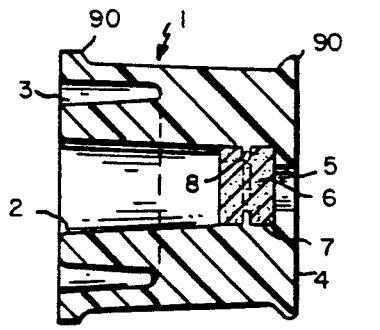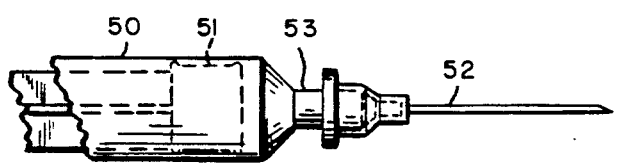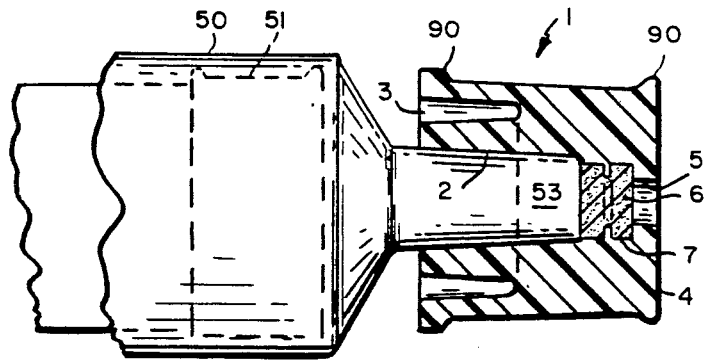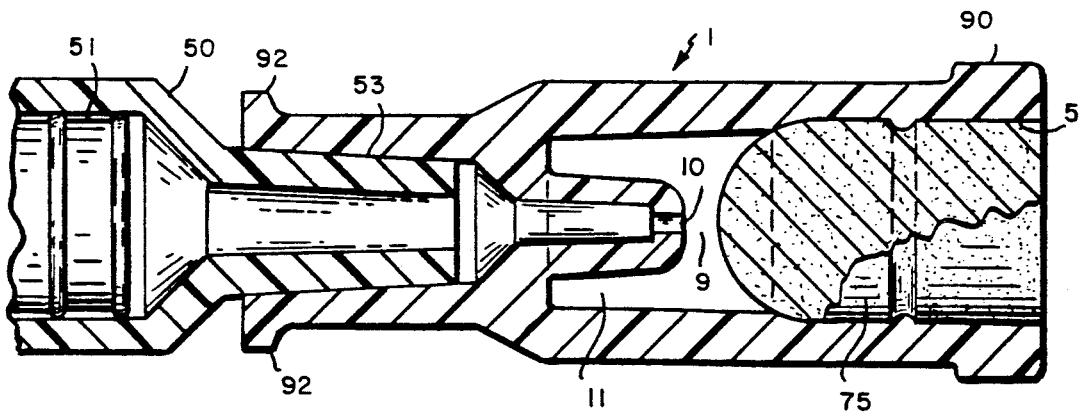

5,125,415

SYRINGE TIP CAP WITH SELF-SEALING FILTER

BACKGROUND OF THE INVENTION

There are many instances in which air can contaminate an arterial blood gas sample. For example, aspiration of a sample through a needle or the incomplete filling of a syringe may draw air into the syringe. Because the purpose of withdrawing the blood is to evaluate the patient's blood gas levels (e.g., carbon dioxide and oxygen) or variables which depend upon blood gas levels (e.g., pH), the introduction of air into the sample would serve to alter the true concentrations in the blood and cause subsequent analysis of data to be misleading.

One technique for removing air from a freshly-filled syringe is to tilt the syringe upward so that air bubbles rise to the top, cradle the open-ended head of the syringe (called the 'luer') with a piece of gauze, and advance the syringe plunger so that air is expelled. Although this technique works well in removing air from the syringe, it may also cause some blood to be expelled. For example, blood may be expelled either if the plunger is pushed too aggressively or if blood is trapped by capillarity in the uppermost portion of the luer. Thus, the present air removal technique poses an unacceptable risk in exposing workers to blood which may contain any number of biohazards.

Most prior art dealing with the air-contamination problem concentrated on expelling contaminating air from the syringe while the syringe was being filled with the patient's blood (Bailey, U.S. Pat. No. 3,978,846; Rattenborg, U.S. Pat. No. 4,340,067; These two systems incorporate hydrophilic filters into the body of the syringe. When dry, a hydrophilic filter allows air to pass through it and out of the syringe. The syringe-filter system fills with blood because a pressure differential between the luer opening and the filter is created by the patient's arterial pressure. This differential helps force air through the filter and out of the syringe. When all of the air is expelled, the leading edge of the blood contacts the filter. When wetted by the blood, the hydrophilic nature of the filter causes it to expand and prohibit passage of both air and liquid. The utility of these hydrophilic systems, however, does not extend to post-filling contaminations because the already-wetted filter will no longer pass air and so it can not be utilized to purge air introduced at later times.

In U.S. Pat. Nos. 4,769,026 and 4,775,376, Strung discloses devices that address the problems of post-filling contamination. These devices utilize separate containers equipped with hydrophobic filters. Hydrophobic filters allow for the passage of air but not liquid. Once the container and syringe are attached in an airtight fit, air and blood from the syringe are injected into this separate container by advancing the syringe plunger until no more air remains in the syringe. There are, however, two weaknesses to this type of system. First, the device's filter will always permit air passage, even when wet. Thus, preparation, transport and handling of the syringe-needle-device unit may engender the threat of air re-entry through the filter. Second, the device uses a rubber stopper to connect the needle of the syringe and the barrel of the device. The disadvantage of this system is that the needle is still connected to the syringe. Thus, preparation, transport, handling and management of the unit may pose unacceptable risks of needle prick.

SUMMARY OF THE INVENTION

The present invention is directed to a syringe tip cap which houses a hydrophilic self-sealing filter in a separate chamber. The tip cap connects with the luer end of a filled syringe. When the blood-air mixture is expelled into the chamber through the luer opening, the air passes quickly through the filter while the blood is taken up by the hydrophilic filter. By the time the filter is blocked by the absorbed blood, all the air has since passed through the filter. The wetted filter forms a seal which prevents subsequent air contamination of the syringe contents. The cap may also include a flow restrictor which limits the flow of blood to only a portion of the filter to prevent premature sealing of the filter.

This new device advantageously allows for flexible management of the syringe in post-filling situations by allowing for needle removal and expulsion of post-filling air. It advantageously uses a hydrophilic filter that does not allow for possible backflow of air into the syringe.

BRIEF DESCRIPTION OF THE DRAWINGS

FIG. 1 is a cross-sectional view of the syringe tip cap of the present invention.

FIG. 2 is a partially sectioned view of a typical syringe.

FIG. 3 is a cross-sectional view of the syringe tip cap of FIG. 1 attached to a typical syringe.

FIG. 4 is a cross-sectional view of an alternate embodiment of the syringe tip cap of the present invention with a partially cross-sectioned filter attached to a typical syringe.

DETAILED DESCRIPTION OF THE PREFERRED EMBODIMENT

Referring now to the drawings, as shown in FIG. 1, the main body of the syringe tip cap is a tubular member 1 of circular transverse cross-section, one end of which is open 2 and fitted on the inside with a groove 3 to accomodate the threaded ring of a luer lock found on some syringes. This end of the member thus defines a fluid-tight connection when it attaches to the male-luer design of a syringe. The other end 4 of the member is virtually closed, except for a vent hole 5 in the middle of the cross-section. Two 360 degree shoulders 90 extend from the virtually closed end 4 of the tubular member 1 and the open end 2 to facilitate handling and manufacturing the syringe tip cap.

Abutting the interior face of the virtually closed end 4 of the tubular member 1 is a disc-like hydrophilic filter 6. The filter is held in place by making it slightly oversized so that it fits the inner wall of the tubular member 7 tightly. Additionally, notches 8 can be placed on the inside surface of the tubular member section which contacts the filter 6 to insure the tight fit.

The filter 6 in the preferred embodiment is comprised of porous polyethylene impregnated with cellulose. It is preferred that the tubular member 1 be made of a non-reactive clear plastic. The clarity of the plastic enables the operator to visually monitor the wetting of the filter 6. The inert quality is necessary because the blood sample's characteristics should not be altered merely by its presence in the tubular member 1.

A syringe 50, shown in FIG. 2, is of standard tubular design fitted with a plunger 51 slidably received therein so that the inside walls of the tube and the outer edge of the plunger 51 produce a tight fit around the circumference of the plunger 51. Typical use of the syringe 50 causes a blood sample to become exposed to a certain amount of air. In order to make use of the syringe cap of the present invention, the needle 52 is unscrewed from the syringe 50 using a sheath after a blood sample has been taken. The syringe tip cap is then screwed onto the luer 53 of the syringe 50. The male luer lock of the syringe securely mates with the female luer lock 3 of the syringe tip cap. Alternatively, the connection can be secured by a friction fit between the outer circumference of the syringe tip and the inner circumference of the cap. Once the syringe tip cap is set securely onto the syringe luer 53, as shown in FIG. 3, an airtight fit is obtained. The syringe is no held so the filter tip cap is pointing up to cause the air to rise to the luer end. The plunger 51 in the syringe 50 is advanced and the air is expelled from the syringe 50 into the syringe tip cap. Because the filter 6 is dry at this time, the air may easily pass through the filter 6 and vent hole 5. Following the air into the syringe tip cap is the leading edge of the blood sample. This blood is pushed forward through the luer 53 and eventually advances all the way u to the filter 6. When the blood contacts the filter 6, the hydrophilic nature of the filter 6 causes it to expand. This expansion serves to prevent air and liquid flow through its axial cross-section. The capped syringe then contains an air free sample sealed against further contamination.

It may be more difficult to expel all of the air if there is blood in the syringe's luer section 53. This blood ('luer blood') is not displaced when the air rises to that end. The luer blood is the first fluid to leave the syringe 50 and contact the filter 6. If the amount of luer blood contacting the filter 6 prior to complete air passage is significant, it may cause the filter 6 to expand and seal off before all the air is purged from the syringe 50.

Referring now to FIG. 4, an improved and preferred tip cap is illustrated. The presently preferred embodiment incorporates a cylindrical axial flow restricter or choke 10 which serves to narrow the flow cross-section of the blood prior to contacting the filter. In addition, the preferred cap also utilizes a convex, or bullet tip, filter 75. This type of filter 75 is configured to reduce the chances of wetting the entire front edge of the filter 75 before all the air is evacuated. Tabs 92 extend outwardly from the tubular member 1. The tabs 92 are used when applicable to engage the threads of a luer lock ring on a syringe.

The more narrow diameter of the choke outlet 10 restricts the area in which the blood initially strikes the filter 75 to a small circumference directly in the middle of the filter 75 cross section. A cavity 9 is formed between the choke output 10 and the filter 75. The cavity 9 is extended down around the circumference of the choke 10 to form a reservoir 11. Thus, the central extended portion of the filter 75 is aligned with the opening in the choke while the recessed portion of the filter, which in this design is the outer annulus, is recessed away from the opening. The recessed portion of the filter is not exposed to liquid as it is expelled from the choke, but only to liquid as the cavity 9 is filled. The reservoir 11 fills with the initial blood expelled from the choke 10, leaving the outer annulus of the filter 75 dry so that air can escape. Thus, when the luer blood is expelled through the choke 10, some may strike the filter 75 and that which does not wet the filter 75 drops to the sides and collects in the reservoir 11. Because the volume of the reservoir 11 is greater than the volume of the syringe's luer volume 53, the reservoir 11 is of sufficient size to collect any of the luer blood which does not initially wet the filter 75. The combination of the reservoir 11 and the choke 10 serves to keep major portions of the filter 75 dry until all the air in the syringe 50 has passed through. Once all the air has passed, the blood from the main body of the syringe 50 enters the syringe tip cap, passes through the choke 10 and into the reservoir 11 and raises the level of blood in the reservoir 11 up to the filter 75. When the cavity 9 is filled with blood, the entire filter 75 surface is wetted and the filter 75 is sealed.

Of course, it should be understood that various changes and modifications to the preferred embodiment described above will be apparent to those skilled in the art. For example, any number of wall shapes, openings and filter configurations may be used to achieve a cap which permits all of the contaminent air to be expelled before all portions of the filter have been sealed. Also, the applicability of the invention need not be restricted to procedures involving blood. Many types of hazardous liquid may be handled by this method. These and other changes can be made without departing from the spirit and scope of the invention and without diminishing its attendant advantages. It is therefore intended that such changes and modifications be covered by the following claims.

I claim:

1. A cap for facilitating purging of gases from a syringe containing hazardous liquids and the gases, comprising:
   a tubular housing which contains
   (a) first and second opposing ends, wherein said first end is open,
   (b) connecting means at said first end of said housing which can form an airtight fit with an open end of the syringe, and
   (c) filter means, consisting essentially of a hydrophilic filter sufficiently thick to prevent liquid from flowing out from said housing, fixed in said housing between said first and second opposing ends.

2. The device as recited in claim 1 wherein the syringe has a male luer lock at its open end and said connecting means comprises a female luer lock.

3. The device as recited in claim 1 wherein the connecting means is the inner circumference of the first end of said housing and wherein said inner circumference forms a friction fit with the outer circumference of the syringe.

4. The device as recited in claim 1 wherein said hydrophilic filter is comprised of porous polyethylene impregnated with cellulose.

5. The device of claim 1 wherein said hydrophilic filter is formed with a convex face facing said first end.

6. The device of claim 1 wherein said housing contains at least one vent hole on said second end.

7. The device of claim 1 further comprising means within said housing for preventing the liquid from completely wetting said filter means before all the gas is purged from the syringe.

8. The device of claim 1 wherein the open end of the syringe is a luer end, said device further comprising:
   (a) a narrowed cross-section of said housing narrowed with respect to the open first end of said housing to restrict flow of fluid from the open first end, said narrowed cross-section being located between the open first end and said filter means,
   (b) a void space between said narrowed cross-section and said filter means, and (c) a reservoir surrounding said narrowed cross-section volumetrically sufficient to hold all of the liquid in the luer end of said syringe.

9. A capped syringe comprising:
a syringe tube having a concentrically narrowed outlet end;
a plunger reciprocally slidable within said syringe tube;
a cap housing having an open end for receiving the narrowed end of said syringe tube in an airtight fit, an other end with a vent hole and a passageway between the open end and the other end; and
a filter means, consisting essentially of a hydrophilic filter, said filter means secured within said cap housing, having a cross-section which covers the passageway and being sufficiently thick to prevent liquid flow from the open end to said vent hole.

10. The syringe of claim 9 further comprising means, interposed between the open end of said cap housing and said hydrophilic filter, for restricting the flow of fluid from said syringe.

11. The syringe of claim 10 further comprising a reservoir surrounding said restricting means.

12. The syringe of claim 10 wherein said hydrophilic filter has a portion exposed to fluid directly expelled into the passageway through said flow restricting means and other portions exposed to the passageway which are recessed away from said flow restricting means.

13. The syringe of claim 10 wherein said hydrophilic filter is formed with a convex face with a central extended portion aligned with the flow of fluid through said restricting means.

14. The syringe of claim 9 wherein said housing is made from a visually clear material which does not react with blood.

15. The syringe of claim 9 further comprising luer lock tabs about the open end of said cap housing.

16. A filtered syringe cap comprising:
a housing having a vent hole at one end, means for receiving a syringe tip in an airtight fit at an other end and a hollow cavity between said ends;
a hydrophilic filter secured within said housing so as to cover said vent hole, said filter having a face exposed to said hollow cavity; and
means for defining an opening in said other end of said housing such that fluid expelled through said opening and into said hollow cavity is directly aligned with only a portion of the exposed face of said hydrophilic filter;
said hollow cavity extending so as to form a reservoir within said housing surrounding said means for defining an opening, said reservoir configured so as to hold liquid components of the fluid away from the exposed face of said filter after the fluid has been expelled from a syringe through said opening so that portions of said filter remain dry to allow gas components of the fluid to escape until said hollow cavity is filled with the liquid components.

17. The syringe cap of claim 16 wherein the exposed face of said filter has a convex shape with a central extended portion, said central extended portion being the only portion of said hydrophilic filter directly aligned with said opening.

18. The syringe cap of claim 16 wherein said hydrophilic filter is made of porous polyethylene impregnated with cellulose.

19. The syringe cap of claim 16 wherein said housing is made from a material which permits viewing of blood as it fills said hollow cavity.

20. A method for purging gases from an arterial blood gas sample, comprising the steps of:
providing a syringe containing an arterial blood gas sample;
removing a needle from a luer end of said syringe;
attaching a vented cap, bearing a hydrophilic filter within the vent, over the luer end of said syringe;
holding said capped syringe with its capped end above its plunger; and
advancing the plunger within said syringe to expel gas and blood from the luer end of said syringe until the blood causes said filter to become sealed, such that the gas escapes through said filter and the blood is prevented from escaping by said filter.

21. A filtered syringe cap comprising:
a housing having an open end for receiving a syringe in an airtight fit, an other end with a vent hole and a passageway between the open end and the other end;
a hydrophilic filter secured within said housing and having a cross section which covers the passageway so as to prevent liquid flow the open end to said vent hole; and
means, interposed between the open end and said hydrophilic filter, for restricting the flow of fluid from said syringe tip.

22. The syringe cap of claim 21 further comprising a reservoir surrounding said restricting means.

23. The syringe of claim 21 wherein said hydrophilic filter has a portion exposed to fluid directly expelled into the passageway through said flow restricting means and other portions exposed to the passageway which are recessed away from said flow restricting means.

24. The syringe of claim 21 wherein said hydrophilic filter is formed with a convex face with a central extended portion aligned with the flow of fluid through said restricting means.

* * * * *